United States Patent [19]

Tracy et al.

[11] Patent Number: 4,806,609

[45] Date of Patent: Feb. 21, 1989

[54] PYRROLIDONYL ACRYLATE BLOCK POLYMERS

[75] Inventors: David J. Tracy, Lincoln Park; Mohamed M. Hashem, Wayne; Fulvio J. Vara, Chester, all of N.J.

[73] Assignee: GAF Corporation, Wayne, N.J.

[21] Appl. No.: 182,611

[22] Filed: Apr. 18, 1988

Related U.S. Application Data

[62] Division of Ser. No. 020,840, Mar. 2, 1987, Pat. No. 4,760,152.

[51] Int. Cl.$^4$ .................... C08L 71/02; C08L 79/04
[52] U.S. Cl. .................... 526/264; 525/404; 525/426; 526/220; 526/258; 526/263; 526/265
[58] Field of Search .............. 526/220, 258, 263, 264, 526/911; 525/404, 426; 548/551; 546/243; 540/531

[56] References Cited

U.S. PATENT DOCUMENTS

| | | | |
|---|---|---|---|
| 4,223,112 | 9/1980 | Hedrick et al. | 525/426 |
| 4,436,933 | 3/1984 | Diery | 526/911 |
| 4,501,861 | 2/1985 | Woodbrey | 525/408 |
| 4,528,331 | 7/1985 | Knopf et al. | 525/404 |
| 4,644,050 | 2/1987 | Mathias et al. | 528/323 |

*Primary Examiner*—Allan M. Lieberman
*Attorney, Agent, or Firm*—Marilyn J. Maue; Joshua J. Ward

[57] ABSTRACT

(1) Pyrrolidonyl acrylate block polymers having the formula

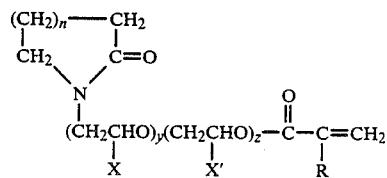

wherein n has a value of 1 to 3; X and X' are dissimilar and each is hydrogen or methyl; y and z each have a value of from 1 to 40, except that at least one of y and z is greater than 1 and R is hydrogen or methyl;
(2) preparation of said polymers and
(3) uses of said polymers.

9 Claims, No Drawings

PYRROLIDONYL ACRYLATE BLOCK POLYMERS

This is a division of application Ser. No. 020,840 filed Mar. 2, 1987, now U.S. Pat. No. 4,760,152.

In one aspect this invention relates to superior emulsifiers for use in the emulsion polymerization of water insoluble monomers. In another aspect the invention relates to an improved emulsion polymerization process and in still another aspect, to novel pyrrolidonyl compounds as well as a method for their preparation.

BACKGROUND OF THE INVENTION

Recently much emphasis has been placed on laminating adhesives, particularly those involving water insoluble polymer, e.g. vinyl polymers, systems which are prepared by emulsion polymerization. There are, however, problems incident to these adhesives, some of which result from the presence of residual surfactant in the resulting composition.

In general, emulsion polymerizations of water insoluble polyesters are well known and involve an emulsifying mixture containing an emulsifying agent, a water insoluble monomer and an inert dispersing liquid in which the monomer is insoluble. The emulsifier maintains the non-agglomerating suspension of monomer and provides a site where polymerization of monomer globules takes place. However, in the course of polymerization small amounts of the emulsifying agent becomes entrapped in the polymeric product, thus presenting problems of subsequent leaching and instability during storage. Additionally, many of these emulsifiers in residual amount cause discoloration on subsequent use.

Moreover, since many of the substrates which are commonly coated with these adhesives are difficult to wet due to their low surface energies, it is generally necessary to post add a surfactant to the adhesive to facilitate wetting of the surface prior to forming the adhesive coat.

Accordingly, it is an object of this invention to overcome the above problems by an economical and commercially feasible process using an improved emulsifying agent.

Another object of this invention is to provide novel compounds having excellent surfactant properties.

Still another object is to provide a process for the manufacture of said novel compounds.

These and many other objects of the invention will become apparent from the following description and disclosure.

THE INVENTION

According to this invention there is provided a group of lactam acrylate block copolymers having the formula

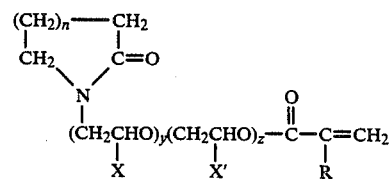

wherein n has a value of from 1 to 3; X and X' are dissimilar and each is hydrogen or methyl; y and z each have a value of from 1 to 40; except that at least one of y and z has a value greater than 1 and R is hydrogen or methyl.

Of the above compounds, those wherein n is 1 and each of y and z has a value greater than 4, are preferred. Most preferred of these compounds are those in which the polyoxypropylene units exceed the number of polyoxyethylene units.

The compounds of this invention are generally prepared according to the following equation:

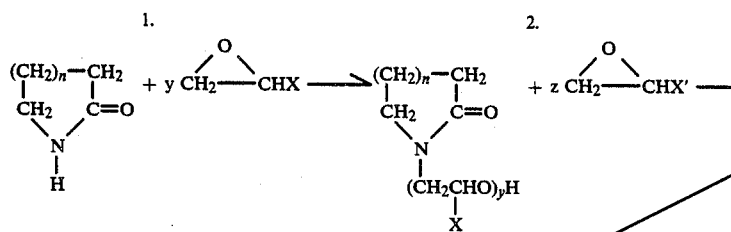
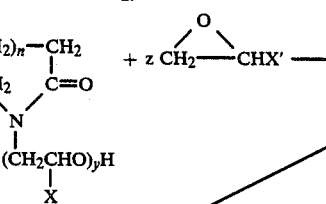

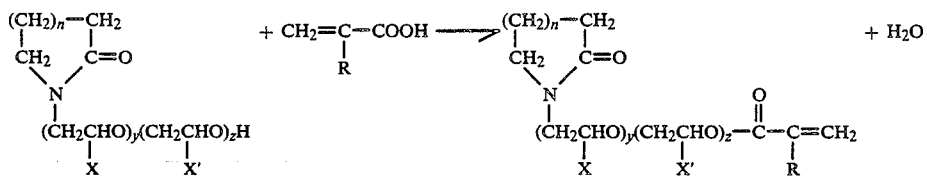

ps where in n, y, z, X, X' and R are as defined above.

More specifically, reactions 1 and 2 are carried out under anhydrous conditions, at a temperature of between about 120° C., and about 180° C. under between about 15 to 80 psig. The reactants in the individual stages (1) and (2) are stirred for a period of between about 10 minutes to about 3 hours at reaction temperature after which, the contents of the respective sealed reactors are cooled and neutralized with a mineral acid such as, for example phosphoric acid, hydrochloric acid, sulfuric acid or a weak organic acid such as acetic acid. Since the above reactions are quantitative, the amount of epoxide reactant in stages (1) and (2), designated by the units y and z, are dependent on the number of units desired in the final block structure. Reaction (1) is preferably effected under slightly alkaline conditions provided by an inorganic hydroxide such as sodium hydroxide, potassium hydroxide, and the like.

As defined above, the epoxide reactants employed in the above equation are ethylene oxide and propylene oxide and the order of their addition depends on the option of the manufacturer and the structure of the product desired.

To produce the final acrylate block polymers of this invention, the intermediate product of reaction (2) is dissolved in a normally liquid, inert solvent such as benzene, toluene, cyclohexane, a $C_8+$ hydrocarbon, etc. to provide a solution containing between about 25 wt. % and about 75 wt. % of the intermediate product. The solution is heated to remove any water which may be present. The solution is then contacted with acrylic acid or methacrylic acid under acidic conditions, in the presence of a antioxidant, radical inhibitor such as p-methoxyphenol, butylated hydroxytoluene, dibutylhydroquinone, catechol and the like. The resulting mixture is then refluxed to remove water in the form of an azeotrope at a temperature of from about 80° C. to about 135° C., preferable from about 100° C. to about 120° C., and unreacted acrylic or methacrylic acid, together with solvent is removed by vacuum stripping at a pot temperature of between about 100° and about 150° C. The process outlined above is effective in producing the present pyrrolidonyl acrylate block polymers in high yield and purity.

The present products possess excellent surfactant and wetting properties and form micelles in solution, hence they are particularly beneficial as emulsifiers for use in the aqueous emulsion polymerization of water insoluble monomers such as sytrene, butadiene, isoprene, vinylidene chloride, acrylonitrile, vinyl chloride and esters such as vinyl- acetate, acrylate and methacrylate which may or may not contain a minor amount, i.e. less than 6% of a water soluble monomer, e.g. acrylic acid.

The present lactams form the interior with their hydrocarbon ends oriented toward the interior of the micelle and their pyrrolidonyl ends extending outward into the dispersing medium. When the monomer is added, its molecules contact the initiator and enter the interior of the micelle. The micelle increases in size as monomer polymerization occurs and the growing polymer reacts with the double bond of the terminal acrylate group of the emulsifier; thus chemically bonding a molecule of the emulsifier to the polymeric backbone. Chemical bonding of the present compounds with the polymerizing water insoluble monomers provides many benefits, among which are the absence of residual leachable emulsifer in the polymeric product and the elimination of emulsifier leaching to the surface of dried polymeric products. The absence of leachable emulsifier also lowers the load on waste water treatment plants.

The polymerization of water insoluble compounds can be carried out using any of the known emulsion polymerization techniques such as those reported in F. A. Bovey et al. "Emulsion Polymerization", Wiley (Interscience) New York, 1955, or summarized in the chapters by J. W. Vanderhoff, W. F. Fowler, Jr. and Harry K. Stryker et al. in G. E. Ham's "Vinyl Polymerization Part II", Marcel Dekker, New York, 1969.

The many parameters of emulsion polymerization technique can be adjusted by those skilled in the art to obtain particular desired results. The comonomers can be added to the aqueous phase gradually or in one charge. Initiator can also be added according to a variety of possible schedules. Thus one or more of the comonomers can be emulsified first in the stirred aqueous phase before initiation is begun, or a saturated solution of a gaseous monomer can be maintained in the presence of surfactant comonomers and of initiator before comonomers are added gradually with or without additional surfactive monomers. Monomers can be added continuously or in staggered increments. Additionally, a polymerization can be started in the presence of a previously prepared seed. Similarly, depending upon the reactivity of the other monomers involved, the polymerizable surfactant may be introduced into the polymerization emulsion at once at the time of polymerization, periodically introducing a part of the polymerizable materials throughout polymerization or continuously introducing a part of the polymerizable materials during the course of the polymerization.

The free radical donors used to initiate the copolymerization can be selected from any of the initiators for aqueous emulsion copolymerization known in the art including those which undergo scission under the influence of heat and those which are caused to form free radicals by reaction with reducing agents. Water-soluble initiators are usually to be preferred including potassium persulfate, ammonium peroxydiphosphate, hydrogen peroxide and others which will be known to those skilled in the art. When reducing agents are used, it is preferred to use water soluble materials such as sodium formaldehyde sulfoxylate, sodium metabisulfite and ascorbic acid. The amounts to be used depend upon the desired rate of polymerization and upon other factors well known in the art. Preferably the aqueous emulsion composition contains between about 0.1 to 10 percent, especially from about 0.2 to 2 percent by weight of initiator. If a reducing agent is used, it also isused in amount totalling between about 0.1 to 5 percent, especially from 0.2 to 2 percent by weight of the finished emulsion. Those skilled in the art will recognize that the amount of initiator used may vary depending upon the particular initiator employed as well as the molecular weight of the polymer desired. Generally the use of higher initiator levels results in polymers of lower molecular weight, and vice-versa.

While reaction temperature of emulsion polymerization can be varied over a wide range, exemplarily using water or oil circulating through jackets or coils for heating and cooling, it is convenient in the case of monomers like vinyl acetate to use reflux condensation as a means of controlling temperature. As to pressure, atmospheric pressure is convenient for many types of copolymerization, but it is suitable to have superatmospheric pressures to confine gaseous monomers like ethylene or butadiene or easily volatile monomers such as vinyl chloride. Pressure is also useful in certain instances to attain desired levels of solubility of monomers in the polymerizing system. Typical elevated pressures vary from about 50 to 150 psi to 10 atmospheres or more. The usual adjustments to control pH, viscosity and other properties can also be used.

The polymerizable surfactant is generally present in the polymer in amounts of about 0.5% to about 6% by weight, preferably about 0.7% to about 3%, although any effective emulsifying amount can be beneficially employed. While other non-polymerizable anionic, cationic or nonionic dispersing agents or surfactants could be used in the polymerization, they should be used only in such small concentrations (i.e. less than about 0.3 to 0.5) that their presence will not have a discernable effect on end use performance. The use of larger amounts which would detract from the properties desired in the final adhesive composition is to be avoided.

The emulsion is generally prepared at a solids content of from about 40% to 65% by weight and, prior to use as a laminating adhesive, it is preferably diluted to a final solids content of from about 15% to 20% for economical reasons. Suitable diluents include water and $C_2$ to $C_4$ aliphatic alcohols.

The high reactivity of the terminal acrylate group in the present surfactants enables their chemical incorporation into the polymer latex, while the lactam ring contributes excellent wetting properties and high affinity for substrates such as metal, wood, concrete or primed or coated surfaces. Accordingly, no external wetting agent need be employed to provide a receptive substrate surface.

The present compounds possess a unique combination of properties. More specifically, the pyrrolidonyl or lactam moiety provides hydrophilic properties; the ethylene oxide - propylene oxide segment contributes lowering of interfacial tension and finally the terminal acrylate group presents a highly reactive polymerizable site on which copolymerization with dissimilar monomer or monomers can be based.

The pyrrolidonyl moiety also possesses the potential of ring opening during polymer curing for interparticle cross-linking with compounds or polymers containing free carboxyl or amine groups or self cross-linking so as to produce a network of cross-linked sites in a thermosetting film or composition.

The products of this invention are also useful as adhesives or coatings for food packaging, painted surfaces, leather, paper, textiles, wood, plastics and ceramics. The lactam acrylate block polymers can also be incorporated into paint formulations and floor finish coatings since they possess good dispersion properties and high resistance to scrubbing with soap and other solvents. Accordingly, such compositions containing from about 0.5 to about 5% by weight of the present compounds are benefited by extended life and shine.

The pigment wetting characteristics of the present compounds make them useful candidates for incorporation into emulsion copolymers such as vinyl acetate/ethyl or butyl acrylate copolymers, butyl acrylate/methylmethacrylate copolymers and 95% vinyl acetate/5% acrylic acid copolymer and enable the pigment to be directed added and uniformly dispersed into the copolymeric emulsions which can be employed as printing inks having superior penetratability.

Having thus generally described the invention, reference is now had to the following examples which are provided to illustrate preferred embodiments but which are not to be construed as limiting to the scope of the invention as more broadly set forth above and in the appended claims.

EXAMPLE 1

Preparation of

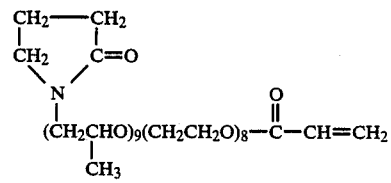

A. To a nitrogen purged autoclave at 150°-160° C. under 22 mm vacuum, was added with stirring 85 . (1.0 mole) of pyrrolidone and 0.5 g. of sodium hydroxide flakes. The vacuum was released by adding 580 . (10.0 moles) of propylene oxide at 160° C.. under 30 psig. The autoclave was held at 160° C. for 1 hour, after which it was cooled to 65 C. and the contents neutralized with 1.1 g. of 85% phosphoric acid. After heating to 85°-90° C. under nitrogen purge to remove water, 634 . of product is discharged. This product was analyzed by NMR (nuclear magnetic resonance spectra) and was found to contain 9.7 moles of propylene oxide.

B. To a nitrogen purged autoclave at 150° C. under 22 mm vacuum, was added 266 . (0.4 mole) of the unneutralized product of 1A with stirring and then 176 g. (4.0 moles) of ethylene oxide was added at 150° C. under 30 psig. The autoclave was held at 160° C. for 30 minutes, after which it was cooled to 65° C. and the contents neutralized to pH 7-8 by the addition of 0.8 g. of 85% phosphoric acid. Water was then removed by heating to 85°-90° C. and the reaction contents purged 30 minutes with nitrogen. The product, 434 g., was then discharged. Analysis by NMR indicated 8.4 moles of ethylene oxide and 9.1 moles of propylene oxide. The cloud point of this product (1B) is 67° C. (1% in water).

C. To a 2 liter round bottom flask, equipped with a stirrer, dropping funnel, thermometer and a modified Dean Stark tube, equipped with a stopcock for removal of water, was charged 500 ml of toluene and 220 g. (0.2 mole) of the produce 1B. Any water was removed after which 0.2 g. of p-methoxyphenol was added followed by 14.4 g. (0.2 mole) of acrylic acid and 1 ml of 100% sulfuric acid. The reaction mixture was then refluxed to remove water azeotrope after which toluene and any unreacted acrylic acid was removed by stripping under 22 mm vacuum at a maximum pot temperature of 120° C. The reacted product, 236.0 g., was recovered and analyzed. Analysis showed carbonyl absorption (ester) at 1735 cm$^{-1}$ and pyrrolidone carbonyl at 1690 cm$^{-1}$, thus indicating the above structure of the product.

EXAMPLE 2

Example 1A, 1B and 1C were repeated except that 0.2 mole of methacrylic acid was substituted in 1C for 0.2 mole of acrylic acid. The product obtained in 2C had the formula

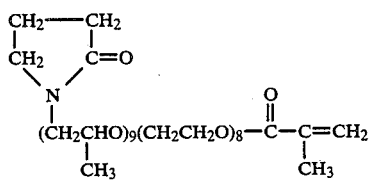

EXAMPLE 3

Preparation of

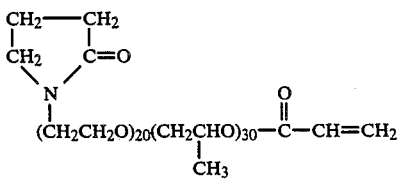

A. To a nitrogen purged autoclave at 150°-160° C. under 22 mm vacuum is added with stirring 85 . (1 mole) of pyrrolidone and 0.5 g. of sodium hydroxide flakes. The vacuum is released by adding 20.0 moles of ethylene oxide at 160° C. under 30 psig. The autoclave is held at 160° C. for 1.25 hours, after which it is cooled to 65° C. and neutralized to pH 7 with 85% phosphoric acid. The reaction mixture is then heated to 85°-90° C. under nitrogen purge to remove water and product 3A, namely

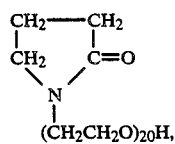

is recovered from the autoclave.

B. To a nitrogen purged autoclave at 150° C. under 22 mm vacuum is added 0.4 mole of the product 3A and 12 moles of propylene oxide were then added at 85 psig. with stirring. The autoclave is held at 160° C. for 30 minutes, after which it is cooled to 65° C. and the contents neutralized to pH 7 with 85% phosphoric acid. Any water is removed by heating to 85°-90° C. and the reaction contents purged for 30 minutes with nitrogen. Product 3B namely

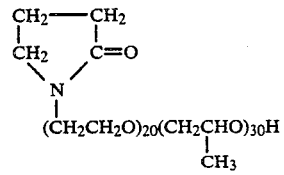

is recovered from the autoclave.

C. To a glass round bottom flask, equipped with a stirrer, dropping funnel, thermometer and a modified Dean Stark tube equipped with a stopcock for removal of water, is charged 500 ml of toluene and 0.2 mole of the product 3B. The procedure described in Example 1C is then repeated to provide the product having the formula

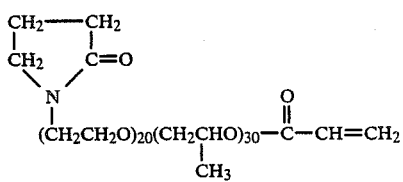

EXAMPLE 4

A 3 liter resin flask is equipped with a paddle stirrer, nitrogen inlet, thermometer and reflux condenser. Deionized water (850 g.), the surfactant product of Example 2 (30 g.), NaHCO$_3$ (4.0 g.) and 5 g. of Natrasol ® 250MXR (hydroxylated ethyl cellulose) were added to the kettle at 65° C. and stirred under a nitrogen atmosphere until dissolved. Sodium persulfate (3.6 g.) was then introduced followed by a mixture of vinyl acetate (872 g.) and butyl acrylate (154 g.) which was added over a period of 4 hours. The temperature was allowed to rise from 65° to 75° C. during the addition of the monomer mixture. After the monomer mixture had been completely added the reaction temperature was maintained at 75° C. for 30 minutes. Tertiary-butyl hydroperoxide (0.1 g.) was then added to the resulting stable emulsion followed by a 25 ml. 2% solution of sodium formaldehyde sulfoxylate which was added over a period of 1 hour while the temperature was maintained at 75° C. The emulsion was cooled and filtered and 100 ppm of coagulum was collected on a 200 mesh screen. The solids content of the filtered emulsion was 55.6% and the viscosity of measured in a Brookfield Viscometer LVT (No. 3 spindle at 60 rpm), was found to be 2200 cps.

The resulting polymer emulsion, containing the present surfactant product, possessed superior surface and pigment wetting properties.

It will become apparent that many modifications and alterations in the foregoing disclosure can be made without departing from the scope of this invention. For example any of the caprolactam block polymeric acrylates or pyridinone block polymeric acrylates can be substituted in the above example illustrating the use of the pyrrolidonyl counterpart as the emulsifer for the polymerization of a water insoluble monomer, to achieve similar benefits due to their high surfactant properties and chemical bondability.

Further either caprolactam or pyridinone can be substituted in step A of Examples 1-3 to produce the corresponding polymeric block acrylates by following steps A, B and C in said examples.

What is claimed is:

1. The process which comprises adding an effective emulsifying amount of the compound having the formula

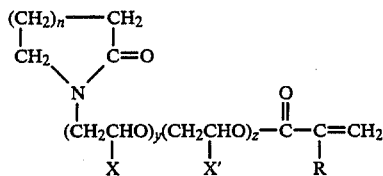

wherein n is an integer having a value of from 1 to 3; X and X' are dissimilar and each of X, X' and R is selected from the group consisting of hydrogen and methyl and y and z are integers each having a value of from 1 to 40, except, when X is methyl, y has a value greater than one and, when X' is methyl, z has a value greater than one, to a water insoluble monomer in an emulsion polymerization mixture containing said monomer, a dispersing medium and polymerization initiator for said monomer.

2. The process of claim 1 wherein said dispersing medium is water.

3. The process of claim 1 wherein said monomer is selected from the group consisting of styrene, butadiene, isoprene, vinylidene chloride, acrylonitrile, vinyl acetate, vinyl chloride, acrylic acid and its esters, vinyl methacrylic acid and its esters and mixtures thereof.

4. The process of claim 1 wherein said compound is added in an amount between about 0.5 and about 6 wt. % with respect to total monomer.

5. The process of claim 1 wherein n of the emulsifying compound has a value of one and each of x and y in the compound of claim 1 has a value of from 6 to 40.

6. The process of claim 5 wherein the number of propylene oxide units exceed the number of ethylene oxide units in said compound.

7. The process of claim 1 wherein n of said compound has a value of one.

8. The process of claim 5 wherein the value of z is greater than the value of y in said compound and X' is methyl.

9. The process of claim 5 wherein the value of y is greater than the value of z in said compound and X is methyl.